United States Patent
Hunter et al.

(10) Patent No.: US 7,189,527 B2
(45) Date of Patent: Mar. 13, 2007

(54) BACTERIAL OXIDATION OF SULPHIDE ORES AND CONCENTRATES

(75) Inventors: Colin John Hunter, Western Australia (AU); Tamsin Lisa Williams, Western Australia (AU); Simon Anthony Roger Purkiss, South Ascot (GB); Leo Wai-Chiu Cheung, New Brunswick (CA); Elena Connors, New Brunswick (CA); Ross David Gilders, New Brunswick (CA)

(73) Assignee: Bioheap Limited, Northbridge (AU)

( * ) Notice: Subject to any disclaimer, the term of this patent is extended or adjusted under 35 U.S.C. 154(b) by 493 days.

(21) Appl. No.: 10/734,581

(22) Filed: Dec. 15, 2003

(65) Prior Publication Data

US 2004/0206208 A1    Oct. 21, 2004

Related U.S. Application Data

(63) Continuation-in-part of application No. 10/070,246, filed as application No. PCT/AU00/01022 on Aug. 29, 2000, now abandoned.

(30) Foreign Application Priority Data

Sep. 3, 1999    (AU) .................................... PQ2651

(51) Int. Cl.
*C12P 39/00*    (2006.01)
*C12P 3/00*     (2006.01)

(52) U.S. Cl. ......................................... 435/42; 435/168

(58) Field of Classification Search ................ 435/42, 435/168
See application file for complete search history.

(56) References Cited

U.S. PATENT DOCUMENTS

| 4,729,788 | A | | 3/1988 | Hutchins et al. |
| 4,888,293 | A | * | 12/1989 | Hackl et al. ................. 435/245 |
| 5,089,412 | A | * | 2/1992 | Hackl et al. ............... 435/252.4 |
| 6,043,022 | A | * | 3/2000 | Lueking et al. ................ 435/3 |
| 6,110,253 | A | * | 8/2000 | Kohr et al. ................... 423/27 |
| H002005 | H | * | 11/2001 | Winby et al. ................. 423/27 |
| 7,022,504 | B2 | * | 4/2006 | Hunter ........................ 435/168 |

FOREIGN PATENT DOCUMENTS

| AU | 714364 B2 | 10/1998 |
| AU | 78560/98 A | 2/1999 |
| WO | WO 9216667 A1 | 10/1992 |
| WO | WO 9428184 A1 | 12/1994 |
| WO | WO 9851827 A1 | 11/1998 |

OTHER PUBLICATIONS

Dopson, M., et al., "Potential role of thiobacillus caldus in arsenopyrite bioleaching", *Applied and Environmental Microbiology*, Jan. 1999, 65:1; 36-40.

* cited by examiner

*Primary Examiner*—Herbert J. Lilling
(74) *Attorney, Agent, or Firm*—Rothwell, Figg, Ernst & Manbeck, PC

(57) ABSTRACT

A process for bacterial oxidation of sulphide ores and concentrates in which the ore or concentrate is leached with a bacterial culture containing one or more strains of both *Sulfobacillus* and *Thermoplasma*.

6 Claims, 1 Drawing Sheet

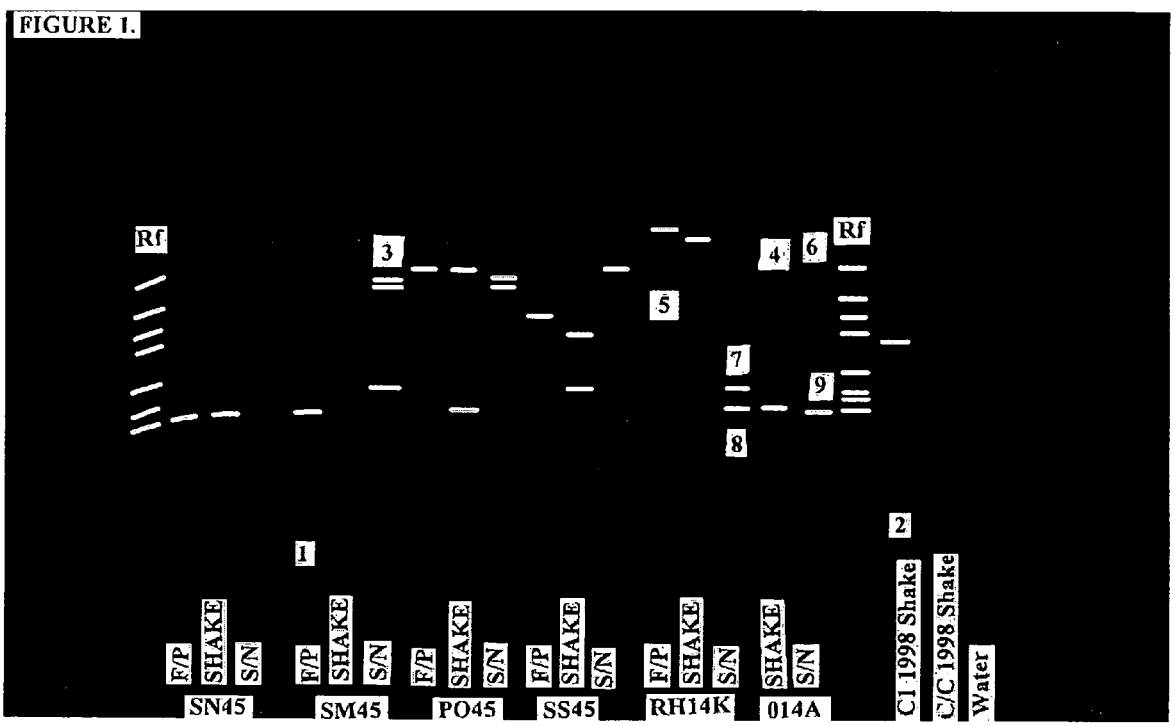

BACTERIAL OXIDATION OF SULPHIDE ORES AND CONCENTRATES

CROSS-REFERENCE TO RELATED APPLICATIONS

This application is a continuation-in-part of application Ser. No. 10/070,246, filed Jun. 26, 2002 (now abandoned), which is a 371 National Stage of International Application No. PCT/AU00/01022, filed Aug. 29, 2000.

FIELD OF THE INVENTION

The present invention relates to the improved bacterial oxidation of sulphide ores and concentrates using a bacterial culture.

The bacterial oxidation process of the present invention has particular application in the bacterial oxidation of ores and concentrates containing chalcopyrite.

BACKGROUND ART

Bacterial oxidation has been used for a number of years in successfully processing arsenopyrite, pyrite, pyrrhotite, covellite and chalcocite ores and concentrates, the one exception to this processing has been the oxidation of chalcopyrite ($CuFeS_2$) ores and concentrates.

Prior art mixes of bacteria used to facilitate oxidation of sulphide ores and concentrates, other than chalcopyrite ores and concentrates, use a variety of suites of bacteria. For example, the mixed bacterial culture employed by Gencor Limited of South Africa comprise predominantly *Thiobacillus ferrooxidans, Thiobacillus thiooxidans* and *Leptospirillum ferrooxidans*. The Gencor cultures consist of a mixed population of mesophilic bacteria, which operate in the temperature range of 35° C. to 45° C. (Dew & Miller, 1997).

Further, Finnish Patent Application 953488 to Gencor Limited discloses the use of *Thiobacillus ferrooxidans, Thiobacillus thiooxidans* and *Leptospirillum ferrooxidans* to achieve oxidation at a pH of preferably 3 with an ore preferably crushed to below 6 mm.

The bacterial culture utilised by BacTech (Australia) Pty Ltd, see for example U.S. Pat. No. 5,429,659, is a moderately thermophilic bacterial culture operating in the temperature range of 46° C. to 50° C. The culture has been designated "M4" by Barrett et al (1988) and has been described by Nobar et al. (1988) (Brierley and Brans 1994).

The MINBAC process developed by Mintek—Anglo American Corporation based in Randburg, South Africa utilises a mesophilic mixed bacterial culture comprising *Thiobacillus ferrooxidans/Leptospirillum ferrooxidans* (Brierley and Brans 1994).

The bacterial cultures presently used are unable to produce commercially acceptable results for chalcopyrite without either ultra fine milling ($P_{80}$<20 μm) of the ore or concentrate to facilitate bacterial oxidation, or the use of very long leach times to achieve oxidation. Times of over 100 days are not uncommon.

Current trends are moving towards the use of higher temperatures to encourage ferric oxidation. However, the high temperatures employed lead to having to cool post-oxidation and to provide reactors formed of specialised materials, for example surgical grade stainless steel. Both circumstances increase the cost of such an operation.

The process of the present has as one object thereof to overcome the above mentioned problems associated with the prior art, or to at least provide a useful alternative thereto.

The preceding discussion of the background art is intended to facilitate an understanding of the present invention only. It should be appreciated that the discussion is not an acknowledgement or admission that any of the material referred to was part of the common general knowledge as at the priority date of the application.

Throughout this specification, unless the context requires otherwise, the word "comprise", or variations such as "comprises" or "comprising", will be understood to imply the inclusion of a stated integer or group of integers but not the exclusion of any other integer or group of integers.

Throughout the specification, reference to a bacterial species is to be understood to include also its sub-species.

Throughout the specification, an ore is considered material that has been removed from the ground and does not receive any treatment to increase the metal concentration. A concentrate is produced by passing an ore through a treatment process, generally gravity or flotation, in order to increase the concentration of desired metals and decrease the volume of material which is subsequently treated to recover those desired metals.

DISCLOSURE OF THE INVENTION

In accordance with the present invention there is provided a bacterial culture for use in the bacterial oxidation of sulphide ores and concentrates, the bacterial culture identified by AGAL deposit Accession No. NM99/07541 or having been adapted therefrom.

In accordance with the present invention there is further provided a process for the bacterial oxidation of sulphide ores and concentrates characterised in that the ore or concentrate is leached using either a bacterial culture identified by AGAL deposit Accession No. NM99/07541 or a bacterial culture adapted therefrom.

In one form of the present invention the sulphide ore or concentrate contains chalcopyrite.

The leach utilised in the process of the present invention may be conducted in a form selected from the group consisting of:

a heap leach,
a tank leach,
a vat leach, and
a dump leach.

The bacterial culture is preferably not indigenous to the ore or concentrate to be oxidised.

The bacterial culture and process of the present invention is effective in the oxidation of sulphide ores or concentrates when the ore or concentrate is provided at a grind or crush size of equal to or greater than $P_{80}$ 90 μm. Preferably, the ore or concentrate is provided at a grind or crush size of equal to or greater than $P_{80}$ 75 μm.

The bacterial culture of the present invention preferably contains at least one or more strains of both *Sulfobacillus* and *Thermoplasma*.

In one form of the invention the culture is operable in the oxidation of sulphide ores and concentrates across a temperature range of 45 to 90° C. Preferably, the culture is operable in the oxidation of sulphide ores and concentrates across a temperature range of 45 to 65° C.

BRIEF DESCRIPTION OF THE DRAWINGS

The present invention will now be described, by way of example only, with reference to the accompanying Figure, in which:

FIG. 1 is a photographic representation of the denaturing gradient gel results for six samples of the bacterial culture of the present invention, processed by three different methods.

DESCRIPTION

In order to raise a culture capable of processing chalcopyrite ores and concentrates a bacterial culture indigenous to a chalcopyrite mineral was sought. Indigenous bacterial cultures are typically superior to modified isolated cultures as the indigenous culture has already been adapted to the toxins and mineral components associated with a particular ore resulting in more effective and resilient bacterial strains.

Bacterial cultures indigenous to chalcopyrite ores were cultivated and tested for their ability to oxidise both their native ore/concentrate and other chalcopyrite ores and concentrates. During this program of work a culture was raised from a chalcopyrite ($CuFeS_2$) concentrate obtained from a base metal ore found in New Brunswick, Canada. Following the isolation of the bacterial culture, testing of the culture has taken place on both its' native ore and concentrate, and on a variety of other ores and concentrates. Additions to the original culture have taken place as, during testing of the culture of different materials, any native bacteria capable of operating under the parameters of the test and being able to operate competitively with the introduced culture have not only survived but have thrived in the environment. In this way any bacteria native to the ore or concentrate being tested have been incorporated into the culture. In addition, the culture has been grown successfully at different temperatures ranging from 40° C. to 90° C. and at varying levels of acidity with pH levels ranging from 0.8–2.2. Successful testing of the culture has taken place in both aerated agitated stirred tank reactors and in aerated columns to facilitate column leaching. Successful testing of the culture took place at a variety of temperatures and on a variety of ores and concentrates.

The bacterial culture of the present invention consists of a variety of iron, sulphide and sulphur oxidising bacteria capable of working at temperatures of up to 65° C. and at pH ranges of between 0.8 and 2.5. The mixed bacterial culture may include, but is not limited to, *Sulfobacillus thermosulfidooxidans, Thiobacillus caldus, Thiobacillus ferrooxidans*, and one or more representatives of the genus *Thermoplasma*, potentially together with a number of as yet unidentified additional bacterial species.

The mixed bacterial culture of the present invention was deposited at the Australian Government Analytical Laboratories (AGAL), The New South Wales Regional Laboratory, 1, Suakin St., Pymble; NSW 2073, Australia, under Accession No. NM99/07541 on Oct. 20, 1999.

EXAMPLE 1

Prior to testing any material the stock bacterial culture is first adapted to the material of interest. This is facilitated by placing 2700 ml of modified OK solution (1.0 g/L ammonium sulphate, 0.5 g/L di-potassium orthophosphate, 0.16 g/L magnesium sulphate heptahydrate, pH 1.6–1.8) into an agitated aerated stirred tank reactor heated to the required temperature. To the modified OK medium a 150 g sample of milled ($P_{80}$<45 µm) test material is added and the pH adjusted down to between 1.6 and 1.8 if necessary using concentrated sulphuric acid. To this slurry a 300 ml slurry sample of the stock inoculum is introduced. The agitated reactor is aerated at a rate of 1 L/min/L slurry. The adaption is continued until the level of relevant metals reporting to solution reaches either 100% or reaches a plateau. Solution samples are assayed for metal levels in solution through the use of an ICP, where appropriate the pH of the slurry is adjusted with concentrated sulphuric acid so that the pH is between 1.6 and 1.8. In addition to metal levels reporting to solution the progress of the adaption/test is further monitored according to its oxidation reduction potential (ORP), ferrous concentration and dissolved oxygen concentration (DO).

Once the culture has adapted to the material of interest it is used as an inoculum for further agitated aerated stirred tank reactor tests or as an inoculum for heap or column tests. The adapted bacterial inoculum is diluted further through the addition of an acidic basic nutrient solution containing ammonium sulphate, potassium orthophosphate and magnesium sulphate. The concentration of these nutrients in solution may vary between laboratory tests and commercial operation and between different commercial operations. In all cases the progress of oxidation is monitored through the levels of metals reporting to solution, pH, ORP, ferrous concentration and DO content.

The bacterial culture of the present invention was tested on a range of chalcopyrite bearing samples from various locations around the world. Table 1 below illustrates the mineralogy and origin of the chalcopyrite concentrates and ores tested using the bacterial culture of the present invention.

TABLE 1

| Sample | Mineralogy | Origin |
|---|---|---|
| A | Chalcopyrite copper concentrate. | USA |
| B | Molybdenum concentrate with low levels of copper in chalcopyrite. | Canada |
| C | Concentrate comprising predominantly chalcopyrite (35%) and cubanite (17%) with lesser quantities of pyrrhotite (10%) and minor amounts of pentlandite (3%) and sphalerite (3%). | Canada |
| D | Copper Nickel concentrate in which copper is present as both chalcopyrite (18.5–28.5%) and cubanite (15.8–30.8%). Nickel is present as pentlandite (17.7–10.4%) and occasionally replaced as violarite. | USA |
| E | Three copper concentrates consisting of chalcopyrite, pyrite and minor amounts of bornite. | Canada |
| F | Copper concentrate consisting of chalcocite (14%), chalcopyrite (10%), bornite (1%) and pyrite (1%). | South Africa |

TABLE 1-continued

| Sample | Mineralogy | Origin |
|---|---|---|
| G | Samples i and iii are ore samples and sample ii is a concentrate sample. The sulphide minerals are predominantly pentlandite, chalcopyrite and pyrrhotite. | Western Australia |

General Test Procedure

All tests on mineral samples were conducted in agitated aerated tank reactors. Each test had a solids density of 10% w/v and was aerated by sparging at a rate of 1 L air per minute per liter of slurry in the reactor. The evaporative losses due to the heating and aeration of the slurry were made up prior to sampling the tests. This was accomplished through the addition of tap water. All slurries were made up in a proprietary nutrient media with a starting pH of 1.0. Sampling involved assaying the solution for iron, copper and other relevant metal ions. In addition, the oxidation-reduction potential (ORP), pH, ferrous iron and dissolved oxygen levels were also monitored and recorded. Copper release was used to monitor the progress of the test and once this reached a stable plateau or attained approximately 100% of the copper reporting to solution the test was deemed complete. Once complete the pulps were pressure filtered, the final leach liquor assayed and the filter cake washed with acidified water and dried. The dried filter cake was weighed and the residue assayed in order to conduct a metallurgical balance.

The results from head analysis, particle size analysis and the results following oxidation are summarised and displayed in Table 2.

TABLE 2

| Sample | Particle Size Analysis | Head Analysis | | | | Results after leaching |
|---|---|---|---|---|---|---|
| | | Fe % | Cu % | $S^{total}$ % | T °C. | Days Leached | % Cu Leached |
| A | $P_{81} < 90$ μm | 28.60 | 29.40 | 32.1 | 48 | 36 | 96.6 |
| B | $P_{85} < 90$ μm | 2.85 | 1.95 | 37.6 | 48 | 20 | 96.9 |
| C | $P_{80} < 75$ μm | 27.30 | 20.97 | 27.37 | 48 | 22 | 98.0 |
| D | $P_{80} < 75$ μm | 26.30 | 12.80 | 25.1 | 48 | 27 | 95.0 |
| E i | $P_{84} < 75$ μm | 15.00 | 2.87 | 13.9 | 48 | 28 | 99.3 |
| E iii | $P_{78} < 75$ μm | 26.6 | 4.62 | 34.4 | 48 | 28 | 99.3 |
| F | $P_{80} < 43$ μm | 6.79 | 28.5 | 10.2 | 60 | 14 | 95.3 |
| G i | $P_{80} < 75$ μm | 17.8 | 1.18 | 7.88 | 48 | 14 | 98.8 |
| G ii | $P_{80} < 75$ μm* | 45.1 | 6.82 | 34.8 | 50 | 10 | 98.0 |
| G iii | $P_{80} < 75$ μm | 18.2 | 0.1 | 3.11 | 50 | 8 | 97.3 |
| H | $P_{80} < 75$ μm* | 23.8 | 19.7 | 36.7 | 48 | 15 | 99.2 |

*nominal sizing of the "as received" concentrate.

A number of samples of the adapted bacterial culture of the present invention have been grown at temperatures ranging generally from 35° C. to 65° C., although the inventors have noted operation at temperatures of up to about 90° C. Samples from each of the cultures have been removed and prepared for identification using 16SrRNA sequencing. Preparation of the samples prior to RNA sequencing was undertaken using three different methods. The methods used and the results obtained from 16SrRNA sequencing are as follows.

Methods

Six samples (designated SN45, SM45, PO45, SS 45, RH 14K, and 014A) were tested.

The samples were mixed on a hand shaker at maximum speed for 30 minutes and processed as follows:

A. Shaken. 500 μl of the shaken sample was immediately sedimented onto glass fibre filters (#30 Sliecher and Schuell, Keene, N.H.) in a 1.5 ml microtube by centrifugation at 14Krpm for 4 minutes. The supernatant was carefully removed, and the sedimented material was washed twice in 1 ml of tissue culture grade water.

B. Fast Prep. 500 μl was immediately removed and homogenized using a Savant BIO 101 Fast Prep machine (BioCan Scientific) at speed 4 for 20 seconds. The homogenates were sedimented and washed as described above.

C. Supernatant. Following shaking, the samples were allowed to sit for 5 minutes to allow the particulate matter to settle to the bottom of the tubes. 500 μl of the supernatant was then sedimented and washed as previously described.

RNA was extracted from all samples using InstaGene Matrix (BioRad, Hercules, Calif.) as per manufacture's instructions. The RNA concentration was determined by uv spectrophotometry ($A_{260}$) and 50 ng were added to the PCR reaction mixture with a final concentration of 2 mM magnesium ion, 100 uM dNTP, 0.32 μm each primer and 0.625 units of Taq Gold Polymerase. The universal primers p515f and p806r (Relman 1993) were used to amplify an approximately 300 bp segment of the 16S ribosomal RNA gene. The forward primer was modified with a 40 bP GC rich sequence that terminated the migration of the amplified product at various concentrations of urea/formamide within a denaturing gradient gel (Sheffield et al. 1989; Muyzer et at. 1993) Bands of interest were cut from the denaturing gels and purified amplified product was subjected to cycle sequencing using Big Dye Terminator extension from the reverse primer using the conditions recommended (PE Applied Biosystems). Sequence determination was performed on a 310 Genetic Analyser (PE Applied Biosystems). Sequence comparisons were conducted using the Basic Local Alignment Search Tool (BLAST; Altschul et al. 1990).

Results

Each of the three samples processing methods resulting in a different profile for the same sample, as shown in FIG. 1. Nine predominant bands were selected for sequencing. The 300 bp segments sequenced had the closest match with partial sequences of the 16S rRNA gene of the bacterial species listed in the BLAST result column. A larger 16S segment would have to be sequenced for more precise identification.

A summary of the BLAST search results for the 300 base pair 16S rRNA gene segments sequenced is shown in Table 3. The numbers in parentheses refer to the % homology between the unknowns and their closest matches.

TABLE 3

| Band | sequenced from | band with same mobility | BLAST result |
|---|---|---|---|
| 1 | SM45-fast prep | SN45-shaken, C1 (1998)-shaken C/C (1998)-shaken | *Sulfobacillus thermosulfidooxidans* (98%) |
| 2 | C1 (1998)-shaken | SM45-fast prep SN45-shaken C/C (1998)-shaken | *Sulfobacillus thermosulfidooxidans* (98%) |
| 8 | RH14K (60° C.)-supernatant | PO45-fastprep/shaken/ supernatant SS45-supernatant | Unidentified bacterium (97%) Denitrifying Fe<II> oxidizing bacteria (97%) |
| 9 | O14A (50° C.)-supernatant | SN45-fastprep/shaken/ supernatant SM45-fastprep O14A shaken | *Thiobacillus ferrooxidans* (96%) |

It is envisaged that bacterial species can be omitted or substituted to the mixed culture outlined above in order to facilitate its operation at different temperatures. For example, *Thiobacillus thiooxidans* a sulphur oxidising bacteria may be substituted for *Thiobacillus caldus* at lower temperatures.

The inventors considered that at least some of the initial results in the characterisation of the bacterial culture of the present invention may have been anomalous. Further work in the characterisation of the bacterial culture of the present invention has been undertaken as follows in Example 2. Over time the accuracy of such characterisation work increases due to improvements in search engines and the updating of databases.

EXAMPLE 2

Methods

Denaturing gradient gel electrophoresis ("DGGE") analysis of 16SrDNA fragments was performed on a sample of the bacterial culture of the present invention. This method, first described by Muyzer et al. (1993), is particularly suitable for profiling complex microbial populations.

Six aliquots of 10 mL of the bacterial culture were centrifuged at ~13,000 g for 15 min. Total sample DNA was extracted from the pellets using a modified version of a previously described method (Plumb et al., 2001). Sample pellets were resuspended in pH 7.2 phosphate buffered saline to initiate cell lysis. Further cell lysis was obtained by treating samples with the lytic enzymes, lysozyme and proteinase K and also the strong detergent sodium dodecyl sulphate (SDS). Following extraction of samples twice with phenol-chloroform-isoamyl alcohol, DNA in solution was precipitated with isopropanol and sodium acetate. Extracted DNA was further purified using the UltraClean™ PCR Clean-up Kit (MO BIO Laboratories Inc.). DNA samples were visualised by staining with ethidium bromide after electrophoresis through a 1% w/v agarose gel.

From each DNA sample, full-length 16S rRNA genes were amplified using the polymerase chain reaction (PCR). PCR primers specific for Bacteria and Archaea were used along with HotStarTaq polymerase (Qiagen) as described previously (Plumb et al., 2002). PCR products were purified using the UltraClean™ PCR Clean-up Kit and then used as template for DGGE PCR reactions. DGGE PCR was performed using previously described primer sets (Muyzer et al., 1993, Øvreås et al., 1997). DNA from three reference strains, *Leptospirillum ferroxidans*, *Sulfobacillus thermosulfidooxidans* and *Sulfolobus* sp. Strain JP2 was also used to generate PCR fragments for DGGE analysis to provide a comparison. DGGE was performed using the DCode™ universal mutation detection system (BioRad Laboratories, USA), and 6% w/v polyacrylamide gels with a denaturing gradient ranging from 30% to 70% (where 100% denaturant contains 7 M urea and 40% v/v formamide). Electrophoreiss was conducted for 16 h at 100 V and 60° C. Gels were stained in 1×TAE buffer containing 0.5 mg $L^{-1}$ ethidium bromide and documented using MultiImage™ light cabinet transilluminator TM-26 (Alpha Innotech Corporation, USA) and ChemiImage V5.5 software. Selected bands were excised from the gels and reamplified using PCR with DGGE primers. Purified PCR products were then sequenced using automated cycle sequencing as described previously (Plumb et al., 2002). Sequence data was analysed using the Basic Local Alignment Search Tool (BLAST, Altschul et aL, 1990) to compare sequences with sequence data in a non-redundant nucleic acid sequence database accessed through http://www.ncbi.nlm.nih.gov/BLAST/.

Results

Examination of the sample using a phase contrast microscope revealed low numbers of small rod-shaped cells. DNA was successfully extracted from each of the six 10 mL samples. The six samples were pooled during the DNA purification step resulting in three purified DNA samples.

From the purified genomic DNA, full-length 16S rDNA was amplified using Bacteria-specific and Archaea-specific primers. This result showed that both Bacteria and Archaea were present. These PCR products were purified and used as templates for PCR amplification of DNA fragments for DGGE analysis. PCR using Bacteria-specific and Archaea-specific DGGE primers successfully amplified DNA fragments for DGGE analysis.

PCR fragments were then subjected to analysis using DGGE to separate DNA fragments according to their electrophoretic mobility through a gel matrix containing increasing concentrations of denaturants. PCR samples from reference strains gave banding profiles as expected. Analysis of the inoculum sample fragment generate using Bacteria-specific primers gave two feint, but distinctive bands. The sample fragment generated using Archaea-specific primers produced only one distinctive band on the gel. The rest of the profile showed non-distinct areas of smeared appearance.

PCR products from bands of interest were sequenced and analysed using BLAST to determine the identity of the DNA sequences. Results of BLAST analyses of the sequence data are summarised in Table 4. Band A contained DNA highly similar (99%) to DNA from strains of the genus *Sulfobacillus*. Bands B and C contained DNA highly similar (98–99%) to DNA from unknown strains of *Thermoplasma*. The genus *Thermoplasma* comprises organisms of the domain Archaea that are characterised by their pleomorphic cell morphology due to the lack of a cell wall and their ability to grow at a range of temperatures from mesophilic to thermophilic. Representatives of the genus are acidophiles capable of growing heterotrophically under aerobic and anaerobic conditions.

TABLE 4

BLAST analysis of sequence data from DNA bands excised from the DGGE profiles of the sample.

| Band Label | Sample Information (primers) | Closest Match (% homology) |
|---|---|---|
| A | Inoculum (Bacteria) | *Sulfobacillus* sp. G2 (99%) |
| B | Inoculum (Baceria) | *Thermoplasma* sp. clone ASL1 (99%) |
| C | Inoculum (Archaea) | *Thermoplasma* sp. clone ASL1 (98%) |

It is unexpected that a bacterial culture having the ability to oxidise sulphide ores and concentrates under the conditions described hereinabove would have representatives of both the genus' *Sulfobacillus* and *Thermoplasma*, with potential for the addition of one or more of the bacterial species identified in Example 1.

It is envisaged that the materials the mixed bacterial culture of the present invention may be used to treat include base metal ores and concentrates (copper, nickel, cobalt zinc etc.), precious metal ores and concentrates (gold and silver) and platinum group metal (PGM) ores and concentrates. It is further envisaged that the culture may be used in a heap leach, tank leach, vat leach or dump leach oxidation.

Heap leaching is by far the most commonly utilised bacterial process for recovering copper from the more easily oxidised secondary copper minerals such as covellite and chalcocite. The process involves stacking crushed ore onto a specially prepared impermeable pad. The pad is designed so that the pregnant liquor draining from the heap collects at a point from which it is drained to a collection pond. Metals are recovered from the pregnant liquor solution either via precipitation, solvent extraction and/or electrowinning.

In order for successful heap leaching to take place it is essential to maintain the integrity of the heap. The main factor determining the heaps stability is the crush size of the ore. Crushing of the ore must take place to an extent where the ore is fine enough to allow good lixiviant percolation through the heap without excessive channelling taking place whilst also maintaining void spaces essential for good air dispersion and lixiviant drainage. If the ore is crushed too finely percolation through the heap may be very slow. Insufficient void spaces will be present and inefficient drainage of the heap will occur resulting in pooling in the heap and a high phreatic head. If on the other hand the ore size is too coarse, drainage of the heap will be fast and the level of metals in solution will be low, in addition the structure of the heap may fail as the ore is broken down through biological and chemical processes. In many cases the crushed ore is agglomerated with binders, sulphuric acid and water prior to stacking, the result being a more uniform particle size and acid distribution throughout the heap.

Prior to stacking the heap a drainage layer is usually placed on the pad, this is generally composed of unreactive rock such as quartzite and ensures adequate drainage of the pregnant liquor. Heaps are irrigated with acidified bacterial liquor which acts as the lixiviant for leaching of the copper from the ore. The bacteria employed in heap leaching are generally aerobic and therefore require oxygen. This may be forced into the heap by means of low pressure blowers or air may be sucked into the heap due to a chimney effect that occurs as bacteria oxidise ore and create heat.

The Geocoat process is a variation on heap leaching and has been marketed by US company Geobiotics. The process involves producing a concentrate from the sulphidic ore, coating this onto crushed, sized rock and producing a heap that can be subjected to bacterial oxidation.

Dump leaching is very similar to heap leaching and is generally reserved for lower grade ores. Often dump leaching will be considered an as accompanying process to heap leaching rather than a stand alone project in its own right. Essentially, where waste or low grade rock is to be mined and stockpiled anyway, with little ground preparation beforehand, some value can be extracted from the material. Indigenous bacteria will be present in the heap and all that is required is to promote their activity. This is done by the addition of acid and nutrients to the irrigation solution, such as with heap leaching. The difference is in the cost.

Little or no crushing will be performed prior to stacking. Only the bare minimum of pad preparation will be performed. There will be no forced aeration.

Vat leaching can be considered to be intermediate between heap leaching and tank leaching in terms of cost, sophistication and efficiency. It is a process in which the material to be treated is fully immersed in the leach solution but is not agitated, at least not to any significant extent, though some agitation due to the air and/or solution flow may take place. The process has the advantage over heap or dump leaching in that complete wetting of the mineral surfaces is achieved and channelling is avoided. Finer crush sizes can also be handled better in a vat, though there is still a limit to the fineness imposed by the need for permeability by both the air and solution. Beyond this limit, it becomes necessary to suspend the material in the solution. If the vats are to be single use only, they can be constructed as lined dams, sloped to one corner to allow circulation and recovery of the leach liquor. Multiple use vats would need to be of a more robust construction such as concrete or brick. Aeration would be by submerged pipe or could otherwise by accomplished by intermittently draining the vat and allowing air to be drawn into the ore by the retreating liquor.

Tank leaching, as the name suggests, entails the bacterial leaching of aerated mineral slurries in agitated tanks. The technology was pioneered by Gencor and is now well developed for the treatment of gold. It is envisaged that the technology would be very similar for base metal bioleaching, but to date a system for copper has not been commercially developed.

Available results indicate that the costs associated with ultra-fine milling of the concentrate ($P_{80}<30$ μm) can be expected to make the capital and operating costs too high.

The bacterial culture and process of the present invention is capable of operating at a wide range of temperatures, thereby leading to a reduction in costs associated with cooling bacterial oxidation systems. The process is further capable of oxidising all forms of chalcopyrite, and at crush sizes that need not incur significant capital and operating costs.

Modifications and variations such as would be apparent to the skilled addressee are considered to fall within the scope of the present invention.

REFERENCES

Altschul, S. F., W. Gish, W. Miller, E. W. Myers, and D. J. Lipman. 1990. Basic local alignment search tool. J. Mol. Bio. 215: 403–410.

Brierley C. L. and R Brans, 1994—Selection of BacTech's Thermophilic Bio-Oxidation Process for Youanmi Mine, In Biomine 94, Conference Proceeding Perth Western Australia. Section 5.

Barrett, J., Hughes, M. N., Ewart, D. K. and Poole, R. K., 1988—The isolation and characterisation of a moderately thermophilic mixed culture of autotrophic bacteria: application of the oxidation of refractory gold concentrates. *Perth Gold* 88, Randol International Ltd, Golden, Colo., pp 148 150.

Dew, D. M. and D. M. Miler, 1997—The BioNIC Process; Bioleaching of Mineral Sulphide Concentrates For Recovery of Nickel, In IBS Biomine '97, Conference Proceedings, Sydney, p M7.1.0–M7.1.9.

Muyzer, G. E. C. DeWall, and A. G. Uitterlinden, 1993. Profiling of complex microbial populations by denaturing gradient gel electrophoresis analysis of polymerase chain reaction amplified genes coding for the 16s rRNA. Appl. Environ. Microbiol. 59: 695–700.

Nobar, A. M., Ewart, D. K., Alsaffar, L., Barrett, J., Hughes M. N. and Poole, R. K., 1988—Isolation and characterisation of a mixed microbial community from an Australian mine: application to the leaching of gold from refractory ores, *Biohydrometallurgy* (P. R. Norris and D. P. Kelly, eds), Science and Technology Letters, Kew Surrey, UK, pp 530–531.

Øvreås, L., Forney, L., Daae, F. I. and Torsvik, V. 1997. Distribution of bacterioplankton in meromictic Lake Saelenvannet, as determined by denaturing gradient gel electrophoresis of PCR-amplified gene fragments coding for 16S rRNA. Applied and Environmental Microbiology, 63, 3367–3373.

Plumb, J. J., Bell, J. and Stuckey, D. C. 2001. Microbial populations associated with treatment of an industrial dye effluent in an anaerobic baffled reactor. Applied and Environmental Microbiology, 67, 3226–3235.

Plumb, J. J, Gibbs, B., Stoll, M. B., Robertson, W. J., Gibson, J. A. E., Nichols, P. D., Watling, H. R. and Franzmann, P. D. 2002. Enrichment and characterisation of thermophilic aidophiles for the bioleaching of mineral sulphides. Minerals Engineering, 15, 787–794.

Relman, D. A. 1993. Universal bacterial 16s rRNA amplification and sequencing, p489–495. In D. H. Persing, T. F. Smith, F. C. Tenover, and J. White (eds) Diagnostic Molecular Biology Principles and Applications—1993. American Society for Microbiology, Washington, D. C.

Sheffield, V. C., D. R. Cox, L. S. Lerman, and R. M. Muyers. 1989. Attachment of a 40 base pair G+C rich sequence (GC-clamp) to genomic RNA fragments by polymerase chain reaction results in improved detection of single base changes. Proc. Natl. Acad. Sci USA 86:232–236.

The invention claimed is:

1. A process for bacterial oxidation of sulphide ores and concentrates characterised in that the ore or concentrate is leached using either a bacterial culture identified by AGAL deposit Accession No. NM99/07541or a bacterial culture adapted therefrom.

2. A process according to claim 1, characterised in that the sulphide ore or concentrate contains chalcopyrite.

3. A process according to claim 1, characterised in that the leach is conducted in a form selected from the group consisting of:
   a heap leach,
   a tank leach,
   a vat leach, and
   a dump leach.

4. A process according to claim 1, characterised in that the bacterial culture is not indigenous to the ore or concentrate to be oxidised.

5. A process according to claim 1, characterised in that the ore or concentrate is provided at a grind or crush size of equal to or greater than $P_{80}$ 75 µm.

6. A process according to claim 1, characterised in that the ore or concentrate is provided at a grind or crush size of equal to or greater than $P_{80}$ 90 µm.

* * * * *